US008887563B2

(12) United States Patent
Lee et al.

(10) Patent No.: US 8,887,563 B2
(45) Date of Patent: Nov. 18, 2014

(54) TRANSDUCER AND METHOD FOR MANUFACTURING SAME

(75) Inventors: Jung Hoon Lee, Seoul (KR); Jae Ha Shin, Seoul (KR); Jun Kyu Choi, Gyeongbuk (KR)

(73) Assignee: Seoul National University R&D Foundation, Seoul (KR)

( * ) Notice: Subject to any disclaimer, the term of this patent is extended or adjusted under 35 U.S.C. 154(b) by 59 days.

(21) Appl. No.: 13/825,045

(22) PCT Filed: Sep. 20, 2010

(86) PCT No.: PCT/KR2010/006466
§ 371 (c)(1),
(2), (4) Date: Mar. 19, 2013

(87) PCT Pub. No.: WO2012/039520
PCT Pub. Date: Mar. 29, 2012

(65) Prior Publication Data
US 2013/0180344 A1 Jul. 18, 2013

(30) Foreign Application Priority Data

Sep. 20, 2010 (KR) ........................ 10-2010-0092282

(51) Int. Cl.
*G01B 21/08* (2006.01)
*G01L 9/12* (2006.01)
*G01N 33/543* (2006.01)
*G01L 1/04* (2006.01)

(52) U.S. Cl.
CPC ... *G01L 1/04* (2013.01); *G01L 9/12* (2013.01); *G01N 33/54373* (2013.01)
USPC .................................. 73/150 A; 73/862.624

(58) Field of Classification Search
CPC ... G01L 1/04; G01L 13/025; G01N 33/54386
USPC ........................................ 73/827, 150 A, 624
See application file for complete search history.

(56) References Cited

U.S. PATENT DOCUMENTS

| 4,238,757 | A | 12/1980 | Schenck |
| 5,466,348 | A | 11/1995 | Holm-Kennedy |
| 6,203,981 | B1 | 3/2001 | Ackley et al. |
| 6,395,557 | B1 * | 5/2002 | Fouillet et al. ................ 436/148 |
| 6,647,796 | B2 | 11/2003 | Beach et al. |
| 7,086,288 | B2 | 8/2006 | Lee et al. |
| 7,568,395 | B2 | 8/2009 | Silverbrook et al. |

(Continued)

FOREIGN PATENT DOCUMENTS

KR    10-2010-0063598    6/2010

OTHER PUBLICATIONS

International Search Report mailed Nov. 28, 2011 for PCT/KR2010/006466.

(Continued)

*Primary Examiner* — Max Noori (57) ABSTRACT

The present invention relates to a transducer and a method for manufacturing same, and more particularly, to a transducer and to a method for manufacturing same, in which a first liquid and a second liquid are supplied such that, at the boundary therebetween, a deformation-generating part, including a perforated structure having one or more holes therein, is formed, and the effect of external pressure is negated by the action between the liquids.

20 Claims, 7 Drawing Sheets

(56) References Cited

U.S. PATENT DOCUMENTS

| | | | |
|---|---|---|---|
| 8,573,297 B2 * | 11/2013 | Tomberlin et al. | 166/254.1 |
| 2004/0096357 A1 | 5/2004 | Majumdar et al. | |
| 2004/0211251 A1 | 10/2004 | Lee et al. | |
| 2005/0064581 A1 * | 3/2005 | Manalis et al. | 435/287.2 |
| 2012/0301893 A1 * | 11/2012 | Siciliano et al. | 435/7.1 |

OTHER PUBLICATIONS

Written Opinion of the International Search Report mailed Nov. 28, 2011 for PCT/KR2010/006466.

* cited by examiner

TRANSDUCER AND METHOD FOR MANUFACTURING SAME

This application claims the priority of Korean Patent Application No. 10-2010-0092282, filed on Sep. 20, 2010 in the KIPO (Korean Intellectual Property Office), the disclosure of which is incorporated herein entirely by reference. Further, this application is the National Stage application of International Application No. PCT/KR2010/006466, filed Sep. 20, 2010, which designates the United States and was published in Korean. Each of these applications is hereby incorporated by reference in their entirety into the present application.

TECHNICAL FIELD

The present disclosure relates to a transducer and a method for manufacturing same, and more particularly, to a transducer which has a first liquid and a second liquid provided with a deformation generating portion having a perforated member shape including one or more holes interposed therebetween as a boundary and removes an effect of an external pressure through an interaction between the liquids, and a method for manufacturing same.

BACKGROUND ART

Hitherto, a transistor (TR)-based biosensor having a structure that includes a transistor has been mainly used among sensors that detect biomolecules using an electrical signal. The biosensor is manufactured by using a semiconductor process and has advantages in that conversion into an electrical signal is fast and a combination of an integrated circuit (IC) and microelectromechanical systems (MEMS) is easily achieved. Therefore, many researches have been conducted on the biosensor.

As an essential patent about measuring a biological reaction using a field-effect transistor (FET), there is U.S. Pat. No. 4,238,757 applied in 1980. This relates to a biosensor measuring a change in a semiconductor inversion layer due to a change in surface charge density in an antigen-antibody reaction as a current and relates to protein among biomolecules.

In U.S. Pat. Nos. 5,466,348 and 6,203,981, contents about improving a signal-to-noise ratio (S/N ratio) using a thin-film transistor (TFT) and combining a circuit is disclosed. However, in order to solve disadvantages of the biosensor using an FET manufactured by the semiconductor process, a biosensor using a thin-film transducer is disclosed.

US Patent Publication No. 2004/0211251 discloses a thin-film transducer type sensor.

The thin-film transducer type sensor uses mechanical stress of a thin-film membrane due to a chemical or biological reaction that occurs in a thin-film connected to an electrode such as gold. That is, a change in capacitance is measured by a change in the distance between the thin-film deformed by the mechanical stress due to the chemical or biological reaction and a lower electrode (this corresponds to a change in the distance between two electrodes), and an analyte is detected from the measured change in capacitance.

Figure 1:
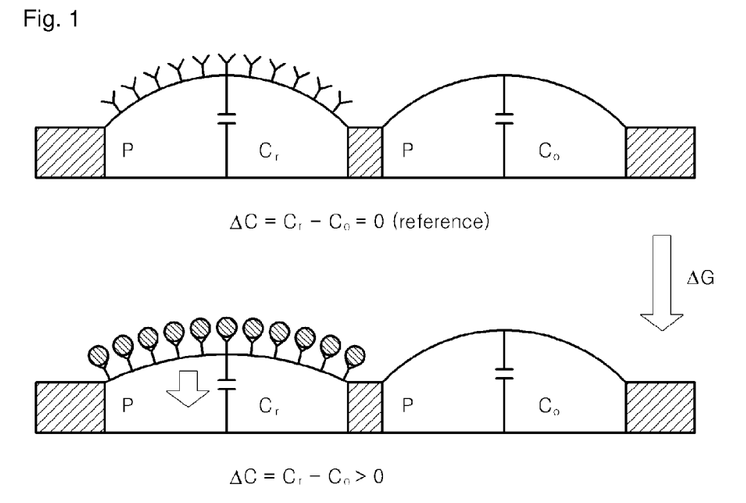
FIG. 1 is a conceptual diagram of a transducer using a thin-film according to the related art.

FIG. 1 is a conceptual diagram of a thin-film transducer disclosed in U.S. Pat. No. 7,086,288. A thin-film surface of the left is treated for a bond with a biomolecule, and a change in capacitance occurs when a biomolecule is bonded thereto.

Here, the change in capacitance includes, in addition to the bond with a biomolecule, an effect of a pressure applied from the outside. In U.S. Pat. No. 7,086,288, a reference thin-film structure is further provided on the right to compensate for the effect of the pressure applied from the outside. Accordingly, the principle that the difference between a change in the capacitance of the thin-film on the left and a change in the capacitance of the thin-film on the right is the same as the difference in the capacitance due to the bond with a biomolecule is used.

In a case of this structure, manufacturing cost of the transducer is increased, an additional system for the difference in capacitance has to be provided, resulting in problems of the complexity of the entire structure, increase in cost, and the like.

DISCLOSURE OF THE INVENTION

Technical Problem

The present disclosure is directed to providing a transducer which reduces an error by removing an effect of a pressure from the outside without providing an additional reference transducer for compensating for a value due to the external pressure.

The present disclosure is also directed to providing a manufacturing method in which an efficiency in a process of removing a sacrificial layer for forming an inner space is increased in a process of manufacturing a transducer.

Technical Solution

In order to solve the above problems, the present disclosure provides the following solution.

In one general aspect, the present disclosure provides a transducer which measures a force applied by an analyte being bonded to a surface thereof, including: a chamber; a deformation generating portion 13 which classifies the chamber into a first area 19 and a second area 17, is provided with a bonding layer 32 to be bonded to the analyte at a surface that comes into contact with the first area 19, and has a perforated member shape including one or more holes that allow the first area 19 and the second area 17 to communicate with each other; a deformation amount measuring member measuring a deformation amount of the deformation generating portion 13; a first liquid 22 which is provided in the first area 19 and includes an analyte; and a second liquid 21 which is provided in the second area 17 and forms an interface with the first liquid 22 in the vicinity of the holes, wherein elastic deformation is generated in the deformation generating portion 13 when the analyte is bonded to the bonding layer 32.

The first liquid 22 may have hydrophilic properties and the second liquid 21 may have hydrophobic properties.

The second liquid 21 may be silicone oil.

The deformation generating portion 13 may be made of a Parylene material.

A surface of the deformation generating portion 13 which comes into contact with the first area 19 may be surface-treated to be hydrophilic and a surface thereof which comes into contact with the second area 17 may be surface-treated to be hydrophobic.

The bonding layer 32 may be made of Au.

The deformation amount measuring member may include an upper electrode 31 provided on a surface which comes into contact with the second area 17 of the deformation generating portion 13 and a lower electrode 33 fixed inside the second area 17 and provided to form capacitance with the upper electrode 31, and may measure capacitance between the upper electrode 31 and the lower electrode 33 according to deformation of the deformation generating portion 13.

The deformation amount measuring member may include an optical sensor 35 measuring a distance from the deformation generating portion 13 and may measure the distance between the optical sensor 35 and the deformation generating portion 13 according to deformation of the deformation generating portion 13.

In another general aspect, the present disclosure provides a transducer which measures a force applied by an analyte being bonded to a surface thereof, including: a chamber; a substrate 10; a deformation generating portion 13 which classifies the chamber into a first area 19 and a second area 17, is provided with a bonding layer 32 to be bonded to the analyte at a surface that comes into contact with the first area 19, and has a perforated member shape including one or more holes that allow the first area 19 and the second area 17 to communicate with each other and being provided on the substrate; a deformation amount measuring member measuring a deformation amount of the deformation generating portion 13; a first liquid 22 which is provided in the first area 19 and includes analyte; and a second liquid 21 which is provided in the second area 17 and forms an interface with the first liquid 22 in the vicinity of the hole, wherein elastic deformation is generated in the deformation generating portion 13 when the analyte is boned to the bonding layer 32.

In another general aspect, the present disclosure provides a method of manufacturing a transducer including: depositing an insulating layer 11 onto a substrate 10; forming a lower electrode 33 on an upper portion of the insulating layer 11; forming a sacrificial layer 12 which covers a part of the insulating layer 11 and a part of the lower electrode 33; forming an upper electrode 31 to extend to an upper portion of the sacrificial layer 12 and to be separated from the lower electrode 33; forming a deformation generating portion 13 to cover the sacrificial layer 12; forming a bonding layer 32 on an upper portion of the deformation generating portion 13; forming a hole which causes the bonding layer 32, the deformation generating portion 13, and the upper electrode 31 to simultaneously communicate with each other; and removing the sacrificial layer 12.

In another general aspect, the present disclosure provides a method of manufacturing a transducer including: forming a lower electrode 33 on an upper portion of a substrate 10; forming a sacrificial layer 12 which covers a part of the substrate 10 and a part of the lower electrode 33; forming an upper electrode 31 to extend to an upper portion of the sacrificial layer 12 and to be separated from the lower electrode 33; forming a deformation generating portion 13 to cover the sacrificial layer 12; forming a hole which causes the deformation generating portion 13 and the upper electrode 31 to simultaneously communicate with each other; and removing the sacrificial layer 12.

The substrate 10 may be made of a silicone material having low resistance.

The lower electrode 33 and the upper electrode 31 may be made of an Au material.

The method may further include filling an inside of the deformation generating portion 13 from which the sacrificial layer 12 is removed with silicone oil.

The deformation generating portion 13 may be made of a Parylene material.

Advantageous Effects

In the present disclosure, there is an effect that the transducer which reduces an error by removing an effect of a pressure from the outside without providing an additional reference transducer for compensating for a value due to the external pressure is provided.

In addition, there is an effect that the manufacturing method in which an efficiency in a process of removing a sacrificial layer for forming an inner space is increased in a process of manufacturing a transducer is provided.

MODE FOR CARRYING OUT THE INVENTION

Embodiments of the present disclosure will be described with reference to the drawings. The following embodiments are examples for describing the present disclosure, and are not intended to limit the present invention to these embodiments. The present disclosure may be implemented in various forms without departing from the gist thereof.

In the description of the present disclosure, in a case where it is determined that detailed description of associated well-known functions and configurations unnecessarily obscure the gist of the present disclosure, the detailed description will be omitted.

The terminology described later is set by considering functions of the present disclosure and may be changed by intensions or practices of users such as an experimenter and a measurer. Therefore, the definitions of the terminology should be determined based on the contents throughout this specification.

A transducer according to the present disclosure is a transducer which measures a force applied by an analyte being bonded to the surface thereof, and includes: a chamber; a deformation generating portion 13 which classifies the chamber into a first area 19 and a second area 17, is provided with a bonding layer 32 to be bonded to the analyte at a surface that comes into contact with the first area 19, and has a perforated member shape including one or more holes that allow the first area 19 and the second area 17 to communicate with each other; a deformation amount measuring member measuring the deformation amount of the deformation generating portion 13; a first liquid 22 which is provided in the first area 19 and includes an analyte; and a second liquid 21 which is provided in the second area 17 and forms an interface with the first liquid 22 in the vicinity of the holes. When the analyte is bonded to the bonding layer 32, elastic deformation is generated in the deformation generating portion 13.

Figure 2:
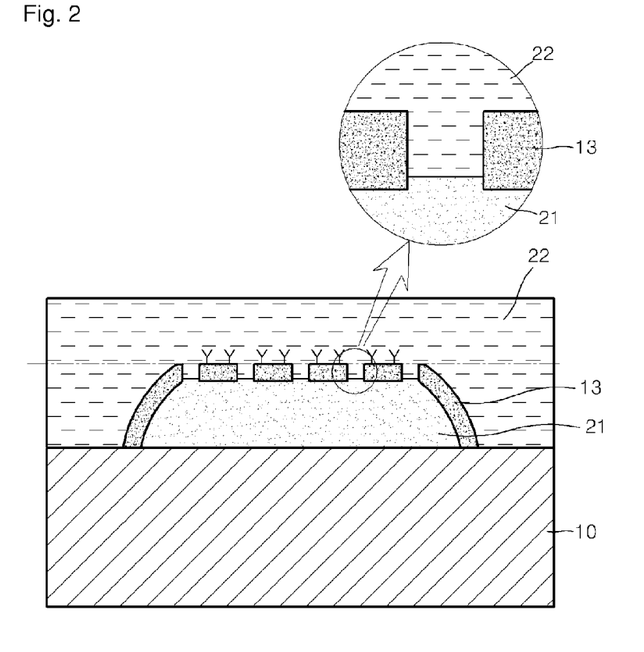
FIG. 2 is a cross-sectional view illustrating a transducer according to the present disclosure before an analyte is bonded.
Figure 3:
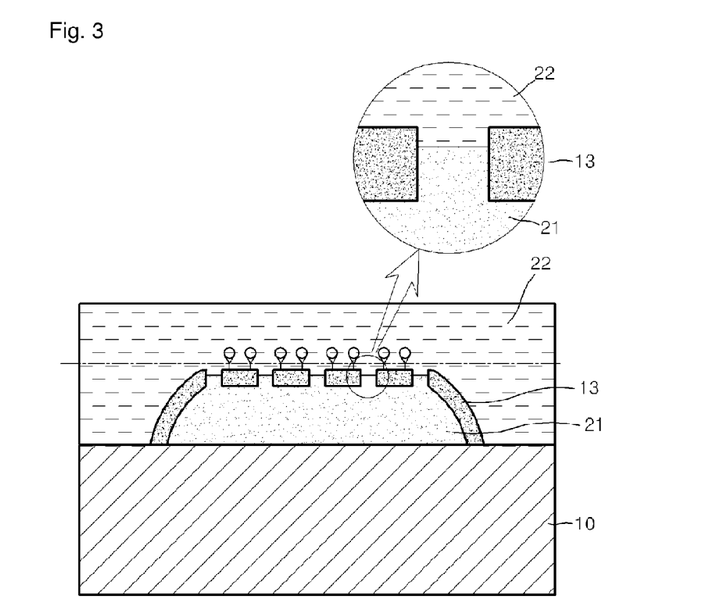
FIG. 3 is a cross-sectional view illustrating the transducer according to the present disclosure after the analyte is bonded.

FIG. 2 is a cross-sectional view illustrating the transducer according to the present disclosure before the analyte is bonded, and FIG. 3 is a cross-sectional view illustrating the transducer according to the present disclosure after the analyte is bonded.

When the analyte is bonded to the bonding layer 32, the deformation generating portion 13 receives stress by a force of interaction due to the analyte, and thus the position thereof is changed.

In a state where the second area 17 is fully filled with the second liquid 21 and is completely closed off from the outside, a pressure difference between the second liquid 21 and the first liquid 22 is generated. Therefore, when an external pressure is generated by the first liquid 22, the second liquid 21 correspondingly receives an effect, which acts as an error in the transducer.

The core of the present disclosure is that the error in the transducer due to the external pressure is removed by removing the pressure difference between the first liquid 22 and the second liquid 21.

For this, holes are formed in the deformation generating portion 13 to cause the first liquid 22 and the second liquid 21 to form an interface in the vicinity of the holes.

This is the principle that when the deformation generating portion 13 is deformed and the size of the second area 17 is changed, the interface between the first liquid 22 and the second liquid 21 is moved around the holes and removes the pressure difference between the two liquids.

Accordingly, the first liquid 22 may have hydrophilic properties, and the second liquid 21 may have hydrophobic properties. Particularly, the second liquid 21 may be silicone oil.

In addition, in the deformation generating portion 13, a surface that comes in contact with the first area 19 may be surface-treated to be hydrophilic, and a surface that comes in contact with the second area 17 may be surface-treated to be hydrophobic.

Figure 4:
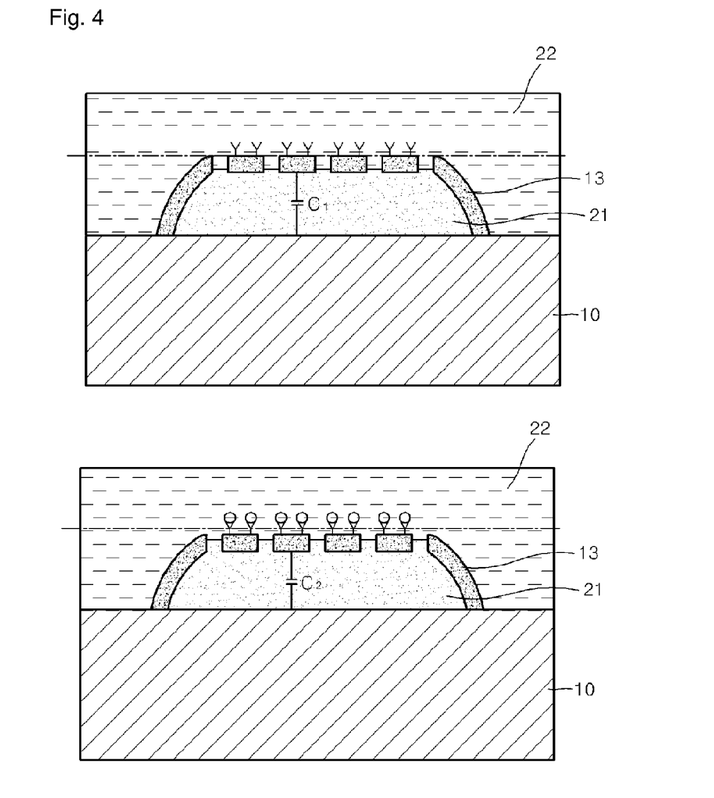
FIG. 4 is a conceptual diagram of a deformation amount measuring method of the transducer according to the present disclosure.
Figure 5:
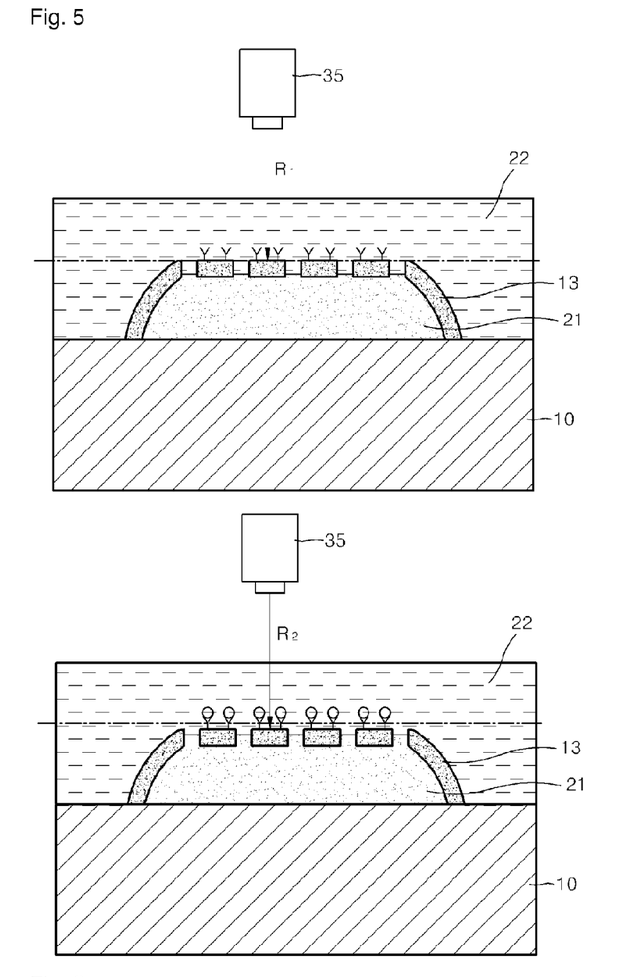
FIG. 5 is a conceptual diagram of a deformation amount measuring method of the transducer according to the present disclosure.

FIGS. 4 and 5 are conceptual diagrams illustrating a deformation amount measuring method in the transducer according to the present disclosure.

For the deformation amount measuring member, both an electric type and an optical type may be used.

In a case of using the electric type, as illustrated in FIG. 4, the deformation amount measuring member includes an upper electrode 31 provided on the surface that comes in contact with the second area 17 of the deformation generating portion 13 and a lower electrode 33 fixed inside the second area 17 and provided to form capacitance with the upper electrode 31, and measures the capacitance between the upper electrode 31 and the lower electrode 33 according to the deformation of the deformation generating portion 13.

As the analyte is bonded to the bonding layer 32, deformation of the deformation generating portion is generated. Accordingly, the distance between the upper electrode 31 and the lower electrode 33 is changed, resulting in a change in the capacitance.

A capacitance value of C1 is exhibited before the analyte is bonded, but is changed to a capacitance value of C2 after the analyte is bonded. The deformation amount of the deformation generating portion may be measured by measuring the amounts of the values C1 and C2 changed, and a force applied to the deformation generating portion (or the amount of analyte boned to the bonding layer) may be calculated by calculating the amounts.

In a case of using the optical type, as illustrated in FIG. 5, an optical sensor 35 which measures a distance from the deformation generating portion 13 is included, and the distance between the optical sensor 35 and the deformation generating portion 13 is measured according to the deformation of the deformation generating portion 13.

In FIG. 5, the optical sensor 35 is positioned above the first area, but the scope of right of the present disclosure is not limited to the position.

Figure 6:
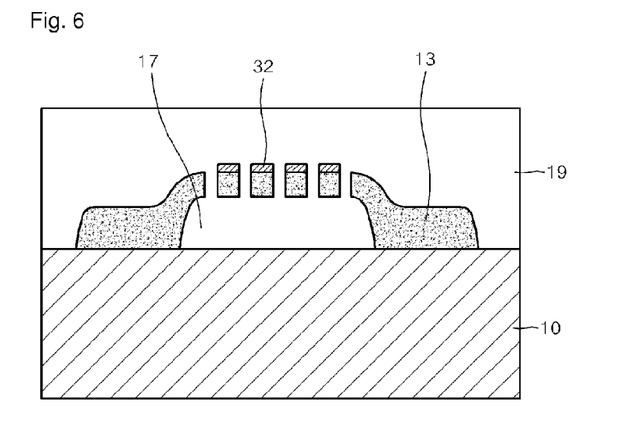
FIG. 6 is a cross-sectional view of an embodiment of the transducer according to the present disclosure.
Figure 7:
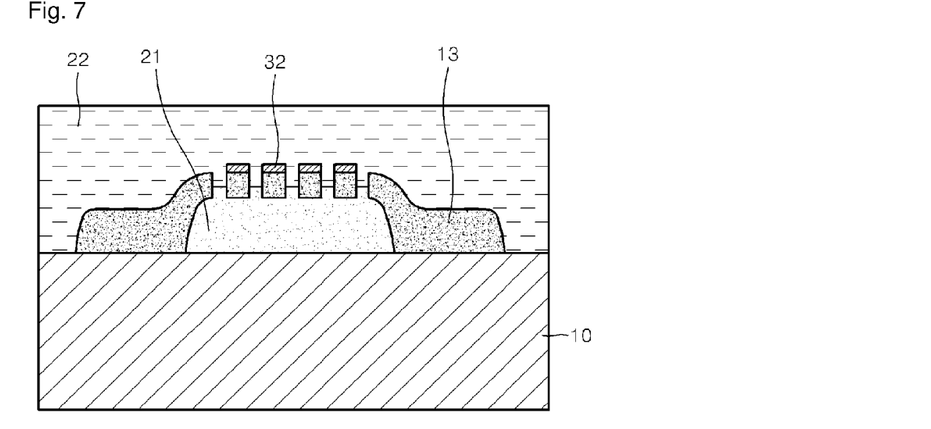
FIG. 7 is a cross-sectional view of an embodiment of the transducer according to the present disclosure.

FIGS. 6 and 7 are cross-sectional views illustrating an embodiment of the transducer according to the present disclosure. The deformation amount measuring member is omitted in the figures.

Figure 8:
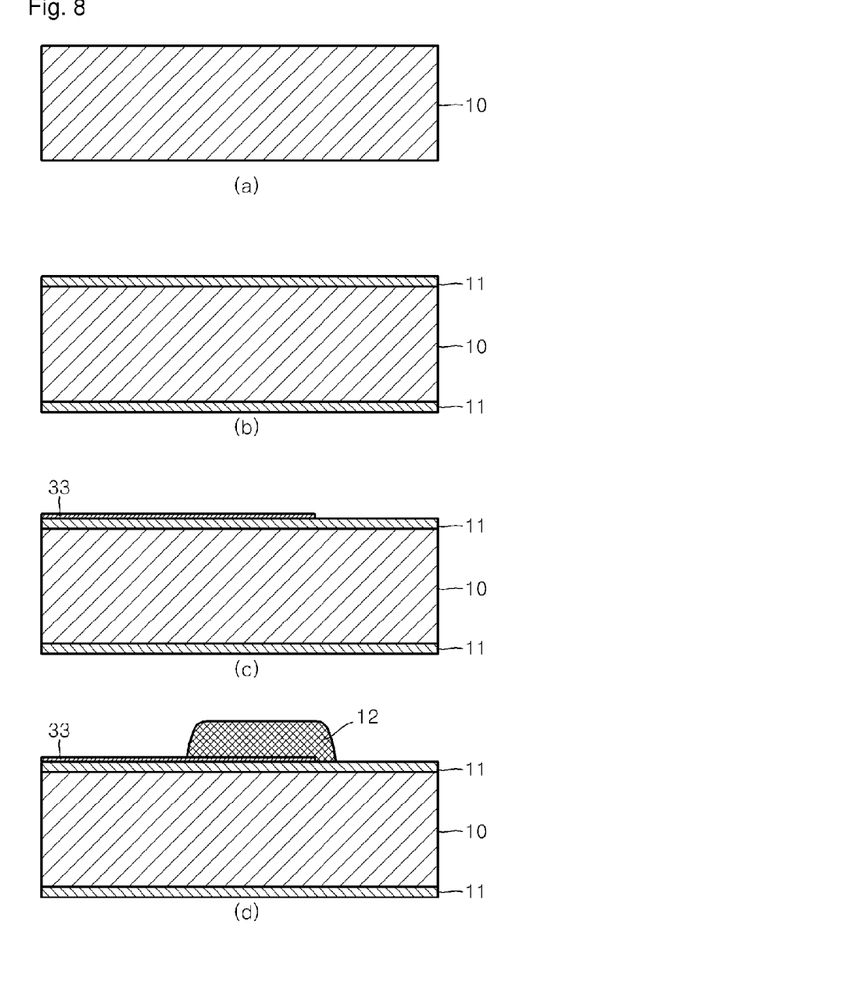
FIG. 8 is a diagram of a manufacturing process of the transducer according to the present disclosure.
Figure 9:
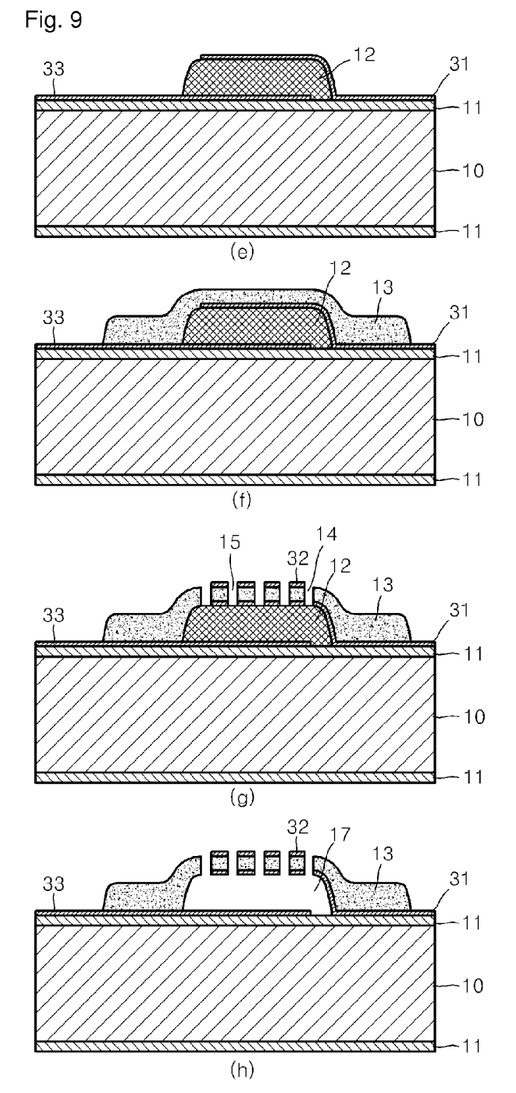
FIG. 9 is a diagram of a manufacturing process of the transducer according to the present disclosure.

FIGS. 8 and 9 are diagrams illustrating a manufacturing process of the embodiment of the transducer which measures the deformation amount of the deformation generating portion by using a capacitance type among the transducers according to the present disclosure. This will be schematically described as follows.

The manufacturing process includes: depositing an insulating layer 11 onto a substrate 10; forming the lower electrode 33 on the upper portion of the insulating layer 11; forming a sacrificial layer 12 which covers a part of the insulating layer 11 and a part of the lower electrode 33; forming the upper electrode 31 to extend to the upper portion of the sacrificial layer 12 and to be separated from the lower electrode 33; forming the deformation generating portion 13 to cover the sacrificial layer 12; forming the boding layer 32 on the upper portion of the deformation generating portion 13; forming the holes which cause the bonding layer 32, the deformation generating portion 13, and the upper electrode 31 to simultaneously communicate with each other; and removing the sacrificial layer 12.

The substrate 10 may be made of a silicon material or glass material having low resistance. In addition, the substrate 10 may be surface-coated to have hydrophobic properties.

The deposition process of the insulating layer 11 may be performed in low-pressure chemical vapor deposition (LPCVD) and plasma-enhanced chemical vapor deposition (PECVD) methods. The insulating layer 11 may be a nitride film for the purpose of preventing the growth of an oxide film in an active area during the growth of an oxide film in a field area in the process of depositing the insulating layer on an initial oxide film.

Here, in a case of a silicon substrate, forming an oxide film may further be included before the deposition process of the insulating layer 11.

The lower electrode 33 is deposited to cause current to flow. The lower electrode 33 may be made of Cr/Au, and may have a Cr thickness of 100 A and an Au thickness of 300 A in a case where the insulating layer has a thickness of 1000 A. The Cr layer is a layer for improving adhesion, and the Au layer is deposited thereon. The deposition may be performed by using an e-gun evaporator method.

The sacrificial layer 12 is for forming an inner space of the transducer later. In the present disclosure, an AZ 5214 photoresist is used, but the present disclosure is not limited thereto. In a case of using the insulating layer and the lower electrode 33, a thickness of 2 m may be used.

The upper electrode 31 functions as a top electrode of the transducer. The upper electrode 31 may also be made of Cr/Au.

The upper electrode 31 influences the thickness and the stress of the deformation generating portion and thus need to have even particle sizes and good adhesion. The upper electrode 31 may be formed in a method similar to that of the lower electrode 33, but a metal sputter deposition method may be used among deposition methods.

The lower electrode 33 and the upper electrode 31 may be provided to overlap each other in parallel with the sacrificial layer 12 interposed therebetween, and the capacitance therebetween is determined by the overlapping area and distance.

The deformation generating portion 13 is made of a polymer material and particularly, may be made of a Parylene material, but the scope of right of the present disclosure is not limited thereto. Parylene is able to be subjected to any process at 200 C or less at the maximum and is thus more advantageous than other materials when low temperature processes are used. In addition, Parylene provides mechanical properties that the deformation generating portion of the transducer requires.

The deformation generating portion 13 is classified into a thin film formed on the upper portion of the sacrificial layer 12 and a thin film supporting portion having a thickness in the periphery of the sacrificial layer 12. The deformation generating portion 13 is provided to completely cover the sacrificial layer 12.

The bonding layer 32 is deposited on the upper portion of the deformation generating portion 13 to be bonded to biomolecules as an example of the analyte. A Cr/Au layer may be used. The biomolecules are bonded to Au metal.

The hole pattern is formed by a positive patterning method. The holes are provided to cause the thin film of the deformation generating portion 13, the upper electrode 31, and the bonding layer 32 to communicate with each other and connect the inside and the outside of the deformation generating portion 13. In a case where there is no bonding layer 32, the holes are provided to cause the deformation generating portion 13 and the upper electrode 31 to communicate with each other.

Thereafter, the upper surface of the thin film is surface-treated to have the hydrophilic properties by a plasma process. Here, since the lower surface of the thin film is protected by the sacrificial layer 12, the hydrophobic properties are continuously maintained. Accordingly, the substrate may be surface-treated to have the hydrophobic properties in advance.

The sacrificial layer 12 is removed by critical point drying method using acetone or methanol as a medium. The sacrificial layer 12 is removed via the holes.

The holes which provided in the deformation generating portion, which are the feature of the present disclosure, also have a function of efficiently removing the sacrificial layer 12 during the process of the critical point drying method.

Finally, the second liquid is filled in the space from which the sacrificial layer 12 is removed. The second liquid may be silicone oil. In a case where the space is not filled with silicone oil, there is a problem in that the analyte flows into the space through the holes. Accordingly, in the present disclosure, in order to solve this problem, the configuration of filling oil is provided.

Figure 10:
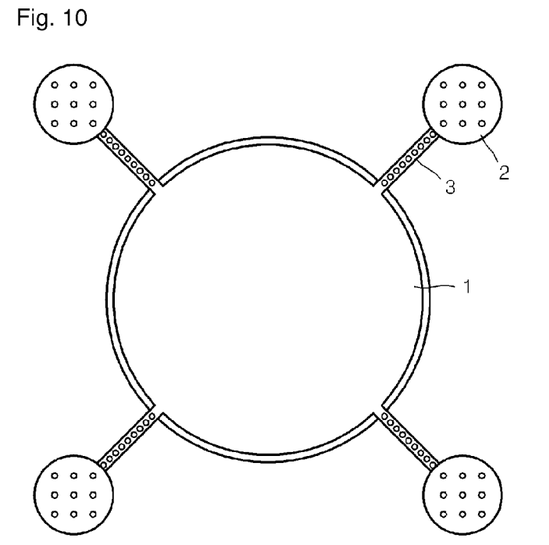
FIG. 10 is a configuration diagram of a structure in which the transducer according to the present disclosure is filled with a second liquid.

FIG. 10 illustrates an embodiment of a structure in which the second space 17 formed in the deformation generating portion 13 is filled with a liquid.

An oil injection portion 1 is provided at the center, and a deformation generating portion structure 2 including a thin film is connected to the oil injection portion 1 with a channel 3. When oil is injected into the oil injection portion 1 after the transducer is put into water, the oil fills the inside of the second space 17 formed in the deformation generating portion structure 2 along the channel 3.

Figure 11:
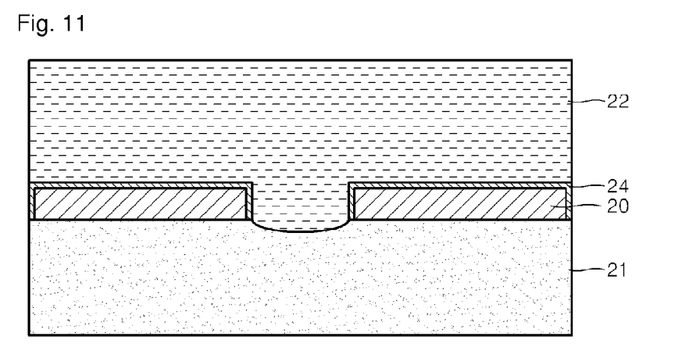
FIG. 11 is a cross-sectional view of a deformation generating portion including holes when the transducer according to the present disclosure is filled with a first liquid and the second liquid.

FIG. 11 is a cross-sectional view illustrating a state in which the inner space of the transducer is filled with the oil. The hole is formed in a part 20 of the deformation generating portion. The upper surface of the part 20 of the deformation generating portion is provided with hydrophilic properties or has a layer 24 for a bond with the analyte. The inside of the deformation generating portion structure is filled with the second liquid 21, and the first liquid 22 is provided outside.

Figure 12:
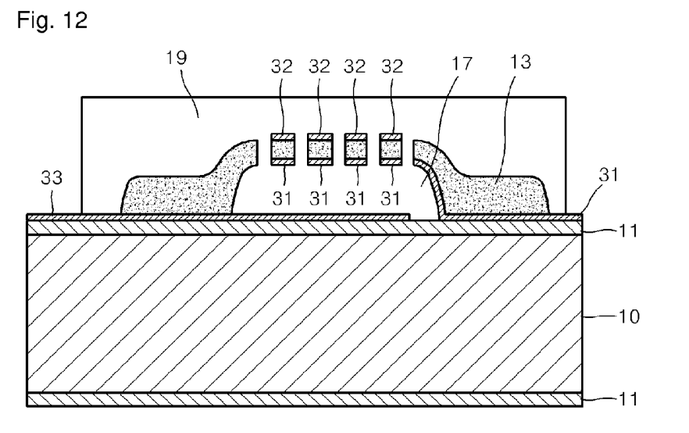
FIG. 12 is a cross-sectional of an embodiment of the transducer according to the present disclosure.

FIG. 12 is a perspective view illustrating the transducer manufactured by the processes described above.

Referring to FIG. 12, the insulating layer 11 is deposited on the upper side of the substrate 10. Here, the insulating layer 11 may be omitted depending on the cases. The upper electrode 31 is formed on the upper side of the substrate 10, and the deformation generating portion 13 is provided to accommodate a part of the upper electrode 31. The lower electrode 33 is formed on the inner surface of the deformation generating portion.

The capacitance is determined by the upper electrode 31 and the lower electrode 33. The boding layer 32 to which an analyte such as biomolecules are bonded is formed on the outer surface of the deformation generating portion 13. The biomolecules are bonded to the boding layer 32, and the surface tension exerted on the deformation generating portion 13 is changed by a force of interaction between the biomolecules. Accordingly, the distance between the upper electrode 31 and the lower electrode 33 is changed, and thus the capacitance is changed.

The amount of biomolecules bonded to the bonding layer 32 is measured by measuring the value of the capacitance changed.

The core of the present disclosure is that at least one or more holes are formed in the deformation generating portion. As described above, the hole has a function of increasing the efficiency in the process of removing the sacrificial layer and also has a function of removing the effect of the external pressure exerted on the deformation generating portion.

That is, in a case where no holes are provided, the deformation generating portion is changed not only by the force of interaction between the biomolecules bonded to the surface of the deformation generating portion, but also by the pressure of the external liquid, and thus there is a high possibility of occurrence of errors.

However, in the case where the holes are provided as in the present disclosure, the pressure difference between the outside and the inside of the deformation generating portion may be removed, and thus there is an effect that the external force due to the pressure of the external liquid and the like may be removed.

Figure 13:
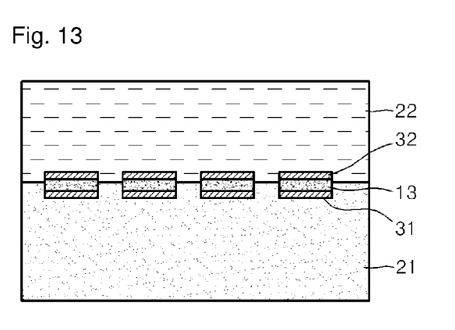
FIG. 13 is a cross-sectional view of the deformation generating portion in the vicinity of the holes of the transducer according to the present disclosure.

Similarly to the above description, in order to prevent the analyte from infiltrating into the deformation generating portion through the holes, the second liquid such as oil is filled. FIG. 13 is a cross-sectional view illustrating the second liquid 21 at the inside and the first liquid 22 at the outside are classified by the deformation generating portion as a boundary.

Consequently, the present disclosure overcomes a disadvantage in that an existing deformation generating portion made of a polymer material such as Parylene receives a large effect due to an external pressure, and furthermore, provides an advantage in that errors due to the pressure effect is removed by forming various hole patterns in the deformation generating portion to achieve a transducer for obtaining more accurate signals and the sacrificial layer is more efficiently removed during the process of the critical point drying method. In addition, by filling the space enclosed by the Parylene structure with silicone oil, an approach of various analytes to the inside may be prevented.

In the present specification, the constituent elements such as Parylene and silicone oil are specifically mentioned, but naturally are substituted with configuration elements capable of providing the same effect. In addition, the scope of right of the present disclosure is not limited to the above embodiments, any modification having the technical spirit of the present disclosure corresponds to the scope of right of the present disclosure, and the scope of right of the present disclosure is determined by the appended claims.

The invention claimed is:

1. A transducer which measures a force applied by an analyte being bonded to a surface thereof, comprising:
   a chamber;
   a deformation generating portion which classifies the chamber into a first area and a second area, is provided with a bonding layer to be bonded to the analyte at a surface that comes into contact with the first area, and has a perforated member shape including one or more holes that allow the first area and the second area to communicate with each other;
   a deformation amount measuring member measuring a deformation amount of the deformation generating portion;
   a first liquid which is provided in the first area and includes an analyte; and
   a second liquid which is provided in the second area and forms an interface with the first liquid in the vicinity of the holes,
   wherein elastic deformation is generated in the deformation generating portion when the analyte is bonded to the bonding layer.

2. The transducer according to claim 1, wherein the first liquid has hydrophilic properties and the second liquid has hydrophobic properties.

3. The transducer according to claim 1, wherein the second liquid is silicone oil.

4. The transducer according to claim 1, wherein the deformation generating portion is made of a Parylene material.

5. The transducer according to claim 1, wherein a surface of the deformation generating portion which comes into contact with the first area is surface-treated to be hydrophilic and a surface thereof which comes into contact with the second area is surface-treated to be hydrophobic.

6. The transducer according to claim 1, wherein the bonding layer is made of Au.

7. The transducer according to claim 1, wherein the deformation amount measuring member includes an upper electrode provided on a surface which comes into contact with the second area of the deformation generating portion and a lower electrode fixed inside the second area and provided to form capacitance with the upper electrode, and measures capacitance between the upper electrode and the lower electrode according to deformation of the deformation generating portion.

8. The transducer according to claim 1, wherein the deformation amount measuring member includes an optical sensor measuring a distance from the deformation generating portion and measures the distance between the optical sensor and the deformation generating portion according to deformation of the deformation generating portion.

9. A transducer which measures a force applied by an analyte being bonded to a surface thereof, comprising:
   a chamber;
   a substrate;
   a deformation generating portion which classifies the chamber into a first area and a second area, is provided with a bonding layer to be bonded to the analyte at a surface that comes into contact with the first area, and has a perforated member shape including one or more holes that allow the first area and the second area to communicate with each other;
   a deformation amount measuring member measuring a deformation amount of the deformation generating portion;
   a first liquid which is provided in the first area and includes an analyte; and
   a second liquid which is provided in the second area and forms an interface with the first liquid in the vicinity of the hole,
   wherein elastic deformation is generated in the deformation generating portion when the analyte is boned to the bonding layer.

10. A method of manufacturing a transducer comprising:
    depositing an insulating layer onto a substrate;
    forming a lower electrode on an upper portion of the insulating layer;
    forming a sacrificial layer which covers a part of the insulating layer and a part of the lower electrode;
    forming an upper electrode to extend to an upper portion of the sacrificial layer and to be separated from the lower electrode;
    forming a deformation generating portion to cover the sacrificial layer;
    forming a bonding layer on an upper portion of the deformation generating portion;
    forming a hole which causes the bonding layer, the deformation generating portion, and the upper electrode to simultaneously communicate with each other; and
    removing the sacrificial layer.

11. The method according to claim 10, wherein the substrate is made of a silicone material having low resistance.

12. The method according to claim 10, wherein the lower electrode and the upper electrode are made of an Au material.

13. The method according to claim 10, further comprising:
    filling an inside of the deformation generating portion from which the sacrificial layer is removed with silicone oil.

14. The method according to claim 10, wherein the deformation generating portion is made of a Parylene material.

15. A method of manufacturing a transducer comprising:
    forming a lower electrode on an upper portion of a substrate;
    forming a sacrificial layer which covers a part of the substrate and a part of the lower electrode;
    forming an upper electrode to extend to an upper portion of the sacrificial layer and to be separated from the lower electrode;
    forming a deformation generating portion to cover the sacrificial layer;
    forming a hole which causes the deformation generating portion and the upper electrode to simultaneously communicate with each other; and
    removing the sacrificial layer.

16. The method according to claim 15, wherein the substrate is made of a silicone material having low resistance.

17. The method according to claim 15, wherein the lower electrode and the upper electrode are made of an Au material.

18. The method according to claim 15, further comprising:
    filling an inside of the deformation generating portion from which the sacrificial layer is removed with silicone oil.

19. The method according to claim 15, wherein the deformation generating portion is made of a Parylene material.

20. The method according to claim 15, wherein the substrate is surface-coated to have hydrophobic properties.

* * * * *